US009830502B2

(12) United States Patent
Cohen et al.

(10) Patent No.: US 9,830,502 B2
(45) Date of Patent: Nov. 28, 2017

(54) METHOD AND SYSTEM FOR CLASSIFYING AND IDENTIFYING INDIVIDUAL CELLS IN A MICROSCOPY IMAGE

(71) Applicant: Molecular Devices, LLC, Sunnyvale, CA (US)

(72) Inventors: Avrum Isaac Cohen, Downington, PA (US); Dihui Hong, Chester City, PA (US)

(73) Assignee: DH Technologies Development Pte. Ltd., Singapore (SG)

(*) Notice: Subject to any disclaimer, the term of this patent is extended or adjusted under 35 U.S.C. 154(b) by 0 days.

(21) Appl. No.: 15/031,523

(22) PCT Filed: Oct. 14, 2014

(86) PCT No.: PCT/US2014/060417
§ 371 (c)(1),
(2) Date: Apr. 22, 2016

(87) PCT Pub. No.: WO2015/065697
PCT Pub. Date: May 7, 2015

(65) Prior Publication Data
US 2016/0259963 A1    Sep. 8, 2016

Related U.S. Application Data

(60) Provisional application No. 61/896,282, filed on Oct. 28, 2013.

(51) Int. Cl.
*G06K 9/62*         (2006.01)
*G06K 9/00*         (2006.01)
(Continued)

(52) U.S. Cl.
CPC .......... *G06K 9/00147* (2013.01); *C12Q 1/04* (2013.01); *G06K 9/0014* (2013.01);
(Continued)

(58) Field of Classification Search
CPC .... G06K 9/66; G06K 9/0014; G06K 9/00147; G06K 9/6263; G06K 9/6267;
(Continued)

(56) References Cited

U.S. PATENT DOCUMENTS 5,987,158 A    11/1999  Meyer et al.
6,134,354 A    10/2000  Lee et al.
(Continued)

FOREIGN PATENT DOCUMENTS

WO    2006099477 A1    9/2006
WO    2013068781 A1    5/2013

OTHER PUBLICATIONS

International Search Report and Written Opinion for PCT/IB2014/060417 dated Jan. 8, 2015.

*Primary Examiner* — Ali Bayat
(74) *Attorney, Agent, or Firm* — McCracken & Gillen LLC (57) ABSTRACT

In a method and system for identifying objects in an image, an image and training data are received. The training data identifies a pixel associated with an object of a particular type in the image. A plurality of filtered versions of the image are developed. The training data and the plurality of filtered versions of the image are processed to develop a trained model for classifying pixels associated with objects of the particular type. The trained model is applied to the image to identify pixels associated a plurality of objects of the particular type in the image. Additional image processing steps are developed to further refine the identified pixels for better fitting of the contour of the objects with their edges.

16 Claims, 7 Drawing Sheets

(51) Int. Cl.
- *C12Q 1/04* (2006.01)
- *G06K 9/46* (2006.01)
- *G06K 9/66* (2006.01)
- *G06T 7/12* (2017.01)
- *G06T 7/13* (2017.01)
- *G06T 7/62* (2017.01)

(52) U.S. Cl.
CPC ......... *G06K 9/4604* (2013.01); *G06K 9/6218* (2013.01); *G06K 9/6256* (2013.01); *G06K 9/6263* (2013.01); *G06K 9/6267* (2013.01); *G06K 9/66* (2013.01); *G06T 7/12* (2017.01); *G06T 7/13* (2017.01); *G06T 7/62* (2017.01); *G06T 2207/10056* (2013.01); *G06T 2207/20081* (2013.01); *G06T 2207/30024* (2013.01)

(58) Field of Classification Search
CPC .. G06K 9/4604; G06K 9/6218; G06K 9/6256; G06T 7/12; G06T 7/13; G06T 2207/10056; G06T 2207/20081; G06T 2207/30024

See application file for complete search history.

(56) References Cited

U.S. PATENT DOCUMENTS

| | | |
|---|---|---|
| 2013/0071003 A1 | 3/2013 | Wirtz et al. |
| 2013/0114874 A1 | 5/2013 | Kask et al. |
| 2013/0329987 A1* | 12/2013 | Gong ................... G06K 9/6269 382/159 |
| 2015/0371115 A1* | 12/2015 | Marchisio ............ G06K 9/6269 382/159 |

* cited by examiner

METHOD AND SYSTEM FOR CLASSIFYING AND IDENTIFYING INDIVIDUAL CELLS IN A MICROSCOPY IMAGE

RELATED APPLICATIONS

This application claims the benefit of U.S. Provisional Patent Application Ser. No. 61/896,282, filed Oct. 28, 2013, the content of which is incorporated by reference herein in its entirety.

TECHNICAL FIELD

This invention relates to processing of images and more particularly identifying individual cells in a microscopy image.

BACKGROUND

A microscopy image of a biological sample may include a variety of cell types and debris against a background. A researcher may want to obtain statistics of a particular type of cell that is present in the microscopy image. Such statistics may include a count of how may cells of the particular cell type are present in the image, the range of sizes of such cells, and the mean, median and mode of the sizes of such cells. Before any such statistics can be calculated, cells of the particular cell type in the microscopy image must be identified from the other cell types present in the microscopy image and also from any debris present in the microscopy image.

Further, to measure the size of a cell, the boundary of such cell may have to be identified. Manually identifying centers and boundaries of all cells of a particular type in an image is time consuming and may lead to fatigue and error on the part of the researcher. Further, the amount of time required to identify and measure cells in a plurality of microscopy images may not be feasible and therefore may limit the type of research that may be conducted.

Edge detection methods have been used to identify edges of objects in an image. However, such methods may not distinguish between objects that are images of cells of a particular cell type, and debris or cells of uninteresting cell types. In addition, such techniques may not be effective in identifying individual cells in images that include a confluent (i.e., adjacent or overlapping) population of cells. Such edge detection techniques may not be effective in identifying cell features, for example, if the contrast between such features and the background is not sufficiently large. Such lack of contrast may be an issue, for example, in images of cells that are not labeled with dyes or other markers. In addition, edge detection methods may not distinguish cells from other types of objects. Further, edge detection methods may not detect the entire edge enclosing an object and provide results that show sections of edges with gaps therebetween instead of an enclosed object.

Other techniques may evaluate an image to identify "bumps" of a particular size and/or shape and combine such bumps with edge information. However, such techniques do not identify irregular shapes well and combining bumps with edge information typically requires significant additional processing time. Graph cuts may be used to distinguish objects in an image from the background. However, this may be computationally intensive and not particularly well suited to processing of real-world images.

As a result, a need exists for an improved approach to identifying and measuring objects in a microscopy image.

SUMMARY

In accordance with one aspect of the invention a computer-implemented method of identifying cells in an image includes receiving an image and receiving training data. The training data identifies a pixel associated with an object of a particular type in the image. The computer-implemented method further includes developing a plurality of filtered versions of the image, and processing the training data and the plurality of filtered versions of the image to develop a trained model for classifying pixels associated with objects of the particular type. In addition, the computer-implemented method includes applying the trained model to the image to identify pixels associated with a plurality of objects of the particular type in the image.

According to another aspect of the invention a system for identifying objects in an image includes an image acquisition module, a user interface module, a filtering module, a training module, and a cell identification module. The image acquisition module receives an image and the user interface module receives training data. The training data identifies a pixel associated with objects of a particular type in the image. The filtering module develops a plurality of filtered versions of the image. The training module processes the training data and the plurality of filtered versions of the image to develop a trained model for classifying pixels associated with objects of the particular type. A cell identification module applies the trained model to the image to identify pixels associated with a plurality of objects of the particular type in the image.

DETAILED DESCRIPTION

Figure 1:
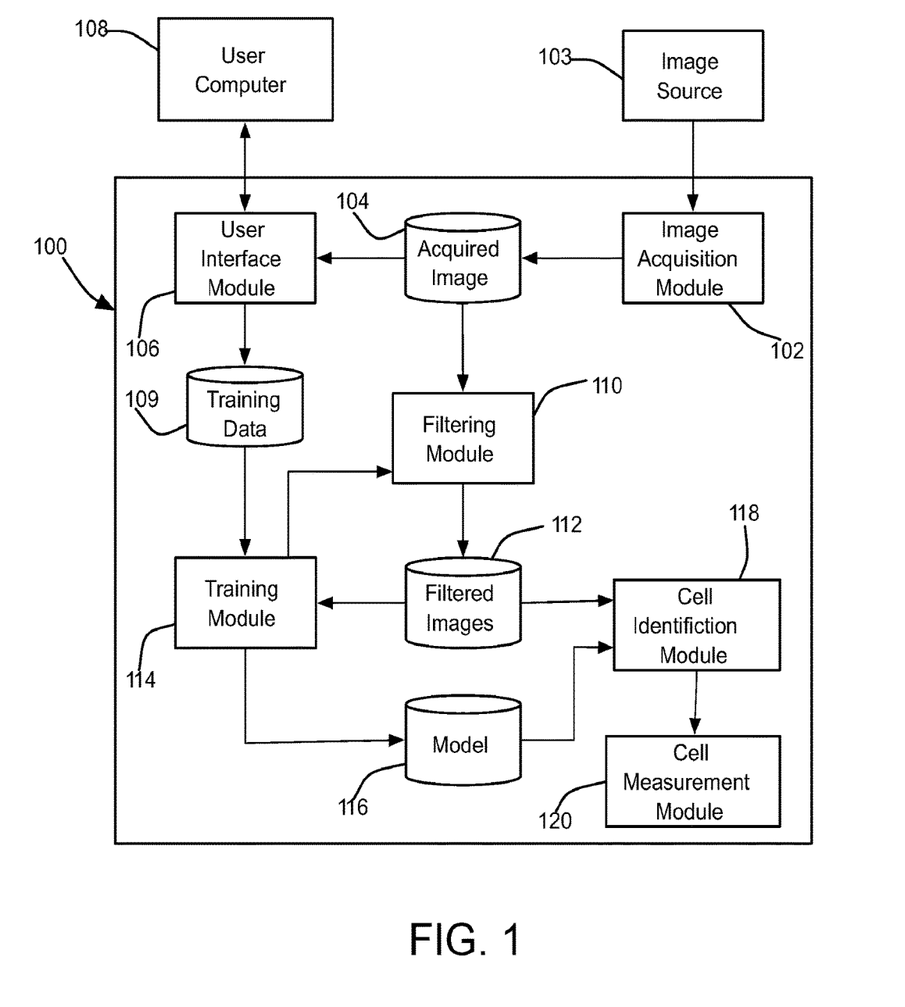
FIG. 1 is a schematic of an object identification system.

Referring to FIG. 1, a cell identification system 100 for processing one or more microscopy images includes an image acquisition module 102 that acquires an image from an image source 103. The image source 103 may be, for example, a microscope, a digital camera, or a repository of previously obtained images. The image acquisition module 102 stores the acquired image in an image store 104.

A user interface module 106 displays the image on a computer 108 operated by a user of the cell identification system 100. Such computer 108 includes a display for displaying information and images transmitted thereto from the cell identification system 100. The computer 108 also includes one or more input devices to provide user selections to the system 100. Such input device includes one or more of a keyboard, a mouse, a touch screen, and the like.

The user uses the input device of the computer 108 to identify one or more areas of the displayed image that are associated with at least one exemplary cell of the particular cell type. The identification may include selecting and marking pixels of the displayed image that are associated with a cell center and/or a cell boundary. In addition, the user may use the input device of the computer 108 to identify one or more areas of the displayed image that are associated with regions that do not have any objects (i.e., the background). The user may also use the input device of the computer 108 to identify one or more areas of the displayed image that are associated with an object, for example, debris, that is not associated with a cell of the particular type.

In one embodiment, the user identifies all of the pixels in the displayed image that are associated with one cell of the particular type. In other embodiments, the user identifies pixels associated with a portion (e.g., a cell center or a cell boundary) of the cell of the particular type. If the user identifies all of the pixels associated with the cell, the user interface module 106 may automatically associate pixels near the outermost pixels of the identified pixels as belonging to the boundary of the cell. In some embodiments, the user interface module 106 may display an image that highlights the pixels of the interior of the cell with a first color and highlights the pixels of the boundary of the cell with a second color and request from the user that such identification is accurate. The user may acknowledge that the identification is correct or adjust the identified cell boundary by selecting the pixels associated with the cell boundary.

The user interface module 106 receives the selections from the computer 108 and develops training data and stores the training data in a training data store 109. In one embodiment, the training data comprises a list of pixel coordinates and an object classification with which such coordinate is associated. The object classification may be one of, for example, cell center, cell edge, unwanted, and the like.

In addition to the training data, the image classification system 100 develops filtered versions of the acquired image. In particular, a filtering module 110 reads the acquired image stored in the acquired image store 104 and applies one or more image filters to the acquired image. The filters that may be applied to the acquired image include an edge detector, a peak detector, a smoothing operator, and the like. The acquired image and the filtered versions of the acquired image are stored in a filtered image store 112.

In addition, the filtering module 110 may apply one or more filters that subsample the image. In addition, the filtering module 110 may apply a plurality of filters to the image in a particular order to develop the filtered image that is stored in the filtered image store 112. For example, the filtering module 110 may apply a subsampling filter and then apply an edge detection filter to the subsampled image and store the resulting edge-detected, subsampled image in the filtered image store 112.

A training module 114 uses the training data, the acquired image and the filtered versions of the acquired image with machine training techniques to develop a trained model that is stored in trained model store 116. The trained model includes a set of rules that can be used to distinguish between pixels in an acquired image that are associated with one or more of, for example, a cell, a cell edge, the background, and the like. Such trained model may be applied to an acquired image and filtered versions thereof to classify the pixels in the acquired image. In one embodiment, the training module 114 uses supervised learning to develop the trained model. Other ways of developing the trained model may be apparent to those who have skill in the art.

In one embodiment, for each coordinate in the training data, the training module 114 evaluates the intensities or strengths of features of the pixel of each image in the filtered image store 112 associated with such coordinate. For example, the training module 114 may determine that a coordinate identified with a cell center in the training data is associated with a first particular intensity in a corresponding pixel in a first filtered version of the acquired image and a second intensity in a corresponding pixel in a second filtered version of the acquired image. Similarly, the training module 114 may determine that background portions of the acquired image are associated with a third intensity in the first filtered version of the acquired image and a fourth intensity in the second filtered version of the acquired image. In another example, the training module 114 may determine that a coordinate associated with a boundary of a cell in the training data is associated with a particular edge direction or edge strength in an edge-detection filtered version of the acquired image.

In this manner, the training module 114 analyzes the acquired image and the filtered image to associate the object classifications in the training model with indications or strengths of features in the acquired image and/or the filtered image to develop a trained model that includes a set of rules that may be applied to an image to classify the pixels in such image as, for example, cell centers, cell edges, background, and the like. Such rules are stored as a trained model in a trained model store 116. In some embodiments, the training module 114 evaluates the rules to determine the effectiveness thereof. The training module 114 applies each rule against the training data and determines the percent of pixels in the training data that are correctly identified using such rule. In some embodiments, from all of the rules generated, the training module 114 may identify a set of rules that are able to correctly classify at least a predetermined percentage of pixels in the acquired image. Such set of rules is stored as a trained model in a trained model store 116 and the remaining rules are discarded. In one embodiment the predetermined percentage is 95 percent. Other predetermined percentages may be selected by the user or in accordance with the types of images being classified.

If the training module 114 discards any of the rules developed thereby, any filtered versions of images that are used only by the discarded rules do not need to be generated when another image is processed using the trained model. In some embodiments, the training module 114 adjusts the filters that will be applied by the filtering module on subsequent images so that the unnecessary filters are not applied. In some embodiments, the training module 114 may determine the filtered images that are used by the rules for classifying pixels of the training data and adjusts the set of filters used by the filtering module 110 accordingly. In particular, the set of filters is adjusted so that the filtering module 110 applies to subsequent acquired images only those filters that are associated with the filtered images used by such rules. Such adjustment of the set of filters applied by the filtering module 110 may reduce the amount of time required of process an image.

In one embodiment the training module 114 applies the trained model developed thereby to the acquired image (and filtered version) to develop a classified version of the acquired image. The classified version of the acquired image identifies (for example, using different colors) pixels determined by the training module to be associated with the centers and boundaries of cells of the particular type. The classified version of the acquired image is displayed on the computer 108 and the user is asked to make any corrections. Such corrections are used to modify the training data and the training module 114 uses the modified training data to refine the trained model. In some embodiments, the system 100 may develop a new trained model from the modified training data. In this manner, the system 100 operates iteratively to refine the trained model until the user is satisfied.

After the trained model is developed and stored in the trained model store 116, the trained model may be applied against a further image acquired by the image acquisition module 102 and stored in the acquired image store 104. The filtering module 110 generates the filtered versions of the further image that are required by the rules that comprise the trained model stored in the trained model store 116. A cell identification module (or object identification module) 118 applies the trained model to the further image and the filtered versions of the further image to classify the pixels of the further image. The cell identification module 118 may develop a version of the further image in which the pixels associated with different parts of the cell are identified. Such image may be viewed by the user on the computer 108 used thereby. In some embodiments, the cell identification module 118 may provide the version of the further image having the classified pixels identified to a cell measurement module 120. The cell measurement module 120 may use techniques that will be apparent to those having skill in the art to develop a count of the cells present in the further images, sizes of such cells, and statistics associated with such cells.

In one embodiment, the cell measurement module 120 selects a group of adjacent pixels (referred herein as a "seed") that have been classified as belonging to a cell. The cell measurement module 120 thereafter grows the seed by adding additional pixels thereto until the cell measurement module 120 determines that the grown seed includes all pixels associated with the cell. In one embodiment, to determine whether a candidate pixel should be added to the seed, the cell measurement module 120 calculates a score by multiplying the distance of the candidate pixel from the original seed and a regulation factor and adding to such product a cumulative sum of absolute values of intensity changes between the original seed and the pixels between original seed and candidate pixel. If the score exceeds a predetermined threshold, the pixel is not added to the seed.

The regulation factor is selected to balance the importance of intensity change versus the distance. If the acquired image has sharp edges and little or no noise, the decision to stop adding pixels to the seed may be based primarily on encountering a candidate pixel associated with an edge (i.e., a substantial change in intensity between the candidate pixel and the rest of the pixels in the seed). If, however, the acquired image has weak edges or has a substantial amount of noise, the regulation factor is selected so that the size of the grown seed controls whether an additional pixel is added to the seed. The cell measurement model 120 analyzes the training data supplied by the user to determine the regulation factor that best grows a seed to match a cell boundary or cell size supplied in the training data. Other ways to select the regulation factor will be apparent to those who have skill in the art.

If a first seed and a second seed associated with a first cell and a second cell are grown as described above and a candidate pixel is identified that can be joined with either seed, a first score and a second score associated with the first seed and the second seed are calculated as described above. The candidate pixel is added to the seed associated with the lower score. Suppose the candidate pixel is added to the first seed because the first score is less than the second score. The first seed may continue to grow as described above until a score is calculated for a further candidate pixel to add to the first seed that is less than the predetermined threshold. In this manner, pixels previously added to the second seed may be removed from the second seed and added to the first seed in accordance with the score calculations described above. In this manner, a pixel that is at a point of equilibrium between the two cells is identified as the best candidate for a pixel belonging to an edge between the two cells. Further, each of the two cells retains its own identity.

In some embodiments, the training module 114 and the cell identification module 118 may be implemented using a Random Forest Decision Tree technique that will be apparent to those having skill in the art. In other embodiments, the training module 114 and the cell identification module 118 may be implemented using other machine learning techniques including, for example, a neural network, support vector machines, k-means clustering, and the like.

In some embodiments, if the user classified only cell centers, only cell centers may be identified after the trained model is applied. In such cases, the cell identification may use the cell center information of each identified cell and select neighboring pixels that also comprise such cell using cell growing techniques that will be apparent to those having skill in the art.

Figure 2A:
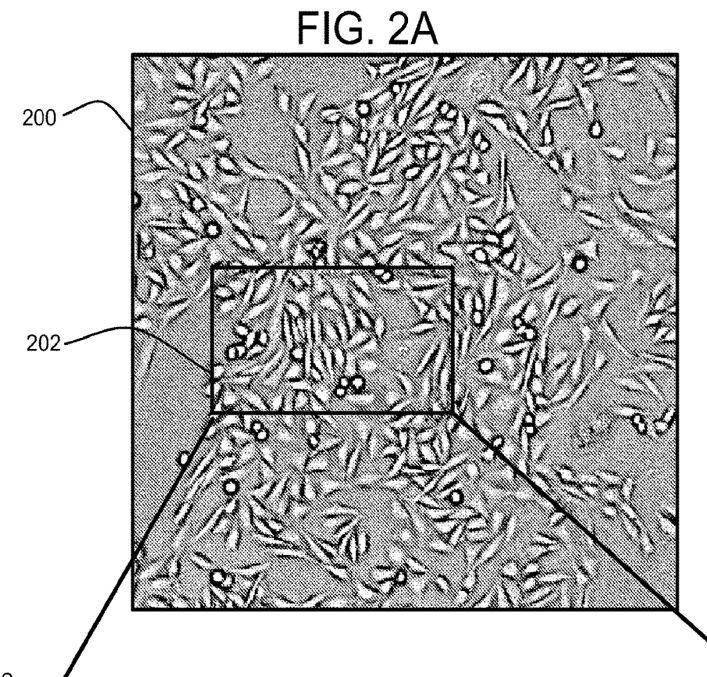
FIGS. 2A and 2B are examples of microscopy images to be processed by the object identification system of FIG. 1.
Figure 2B:
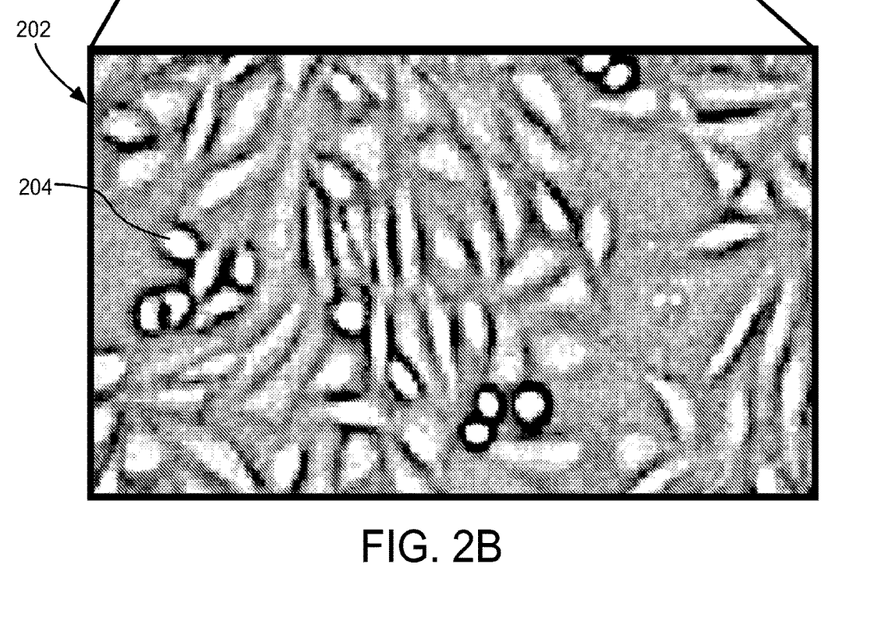

FIG. 2A illustrates an example of a microscopy image 200. A portion 202 of the microscopy image 200 is shown magnified in FIG. 2B. Referring to FIG. 2B, the portion 202 includes cells 204.

Figure 3A:
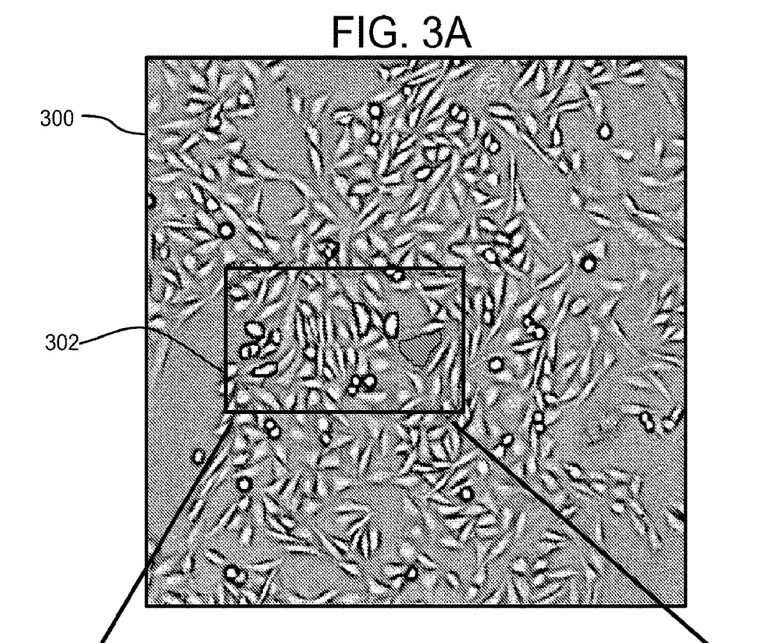
FIGS. 3A and 3B are the images of FIGS. 2A and 2B showing input provided by the user.
Figure 3B:
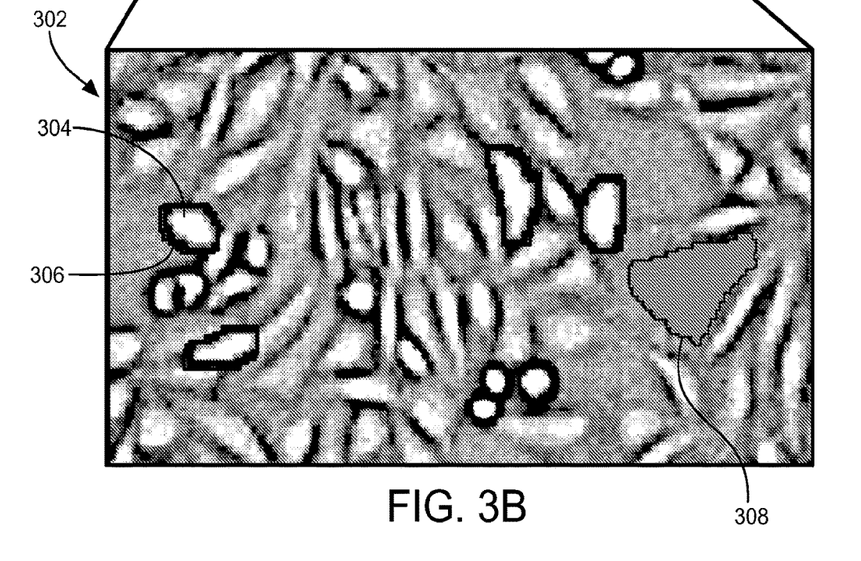

FIGS. 3A and 3B illustrate an example of an image 300 and a portion 302 thereof that show the microscopy image 200 after the user has identified exemplary objects therein. The user has identified a cell center 304 and a cell boundary 306 of the cell 204, and a background area 308. As described above, the cell boundary 306 may be derived automatically by the system 100 if the user identifies the entirety of the cell 204.

Figure 4:
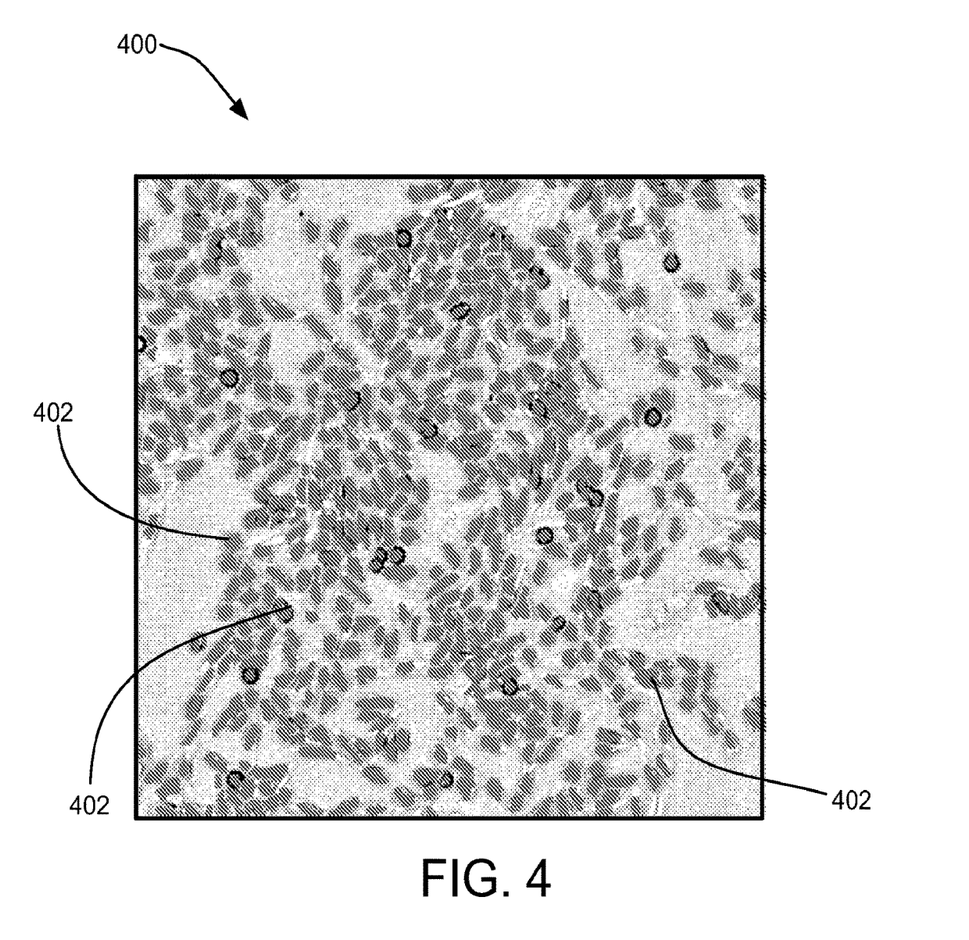
FIG. 4 is an example of an image that results from processing the images of FIG. 2A using the system of FIG. 1.

FIG. 4 illustrates an image 400 that results after the image 200 has been processed as described above. As is apparent, cells 402 throughout the image 400 have been identified.

Figure 5:
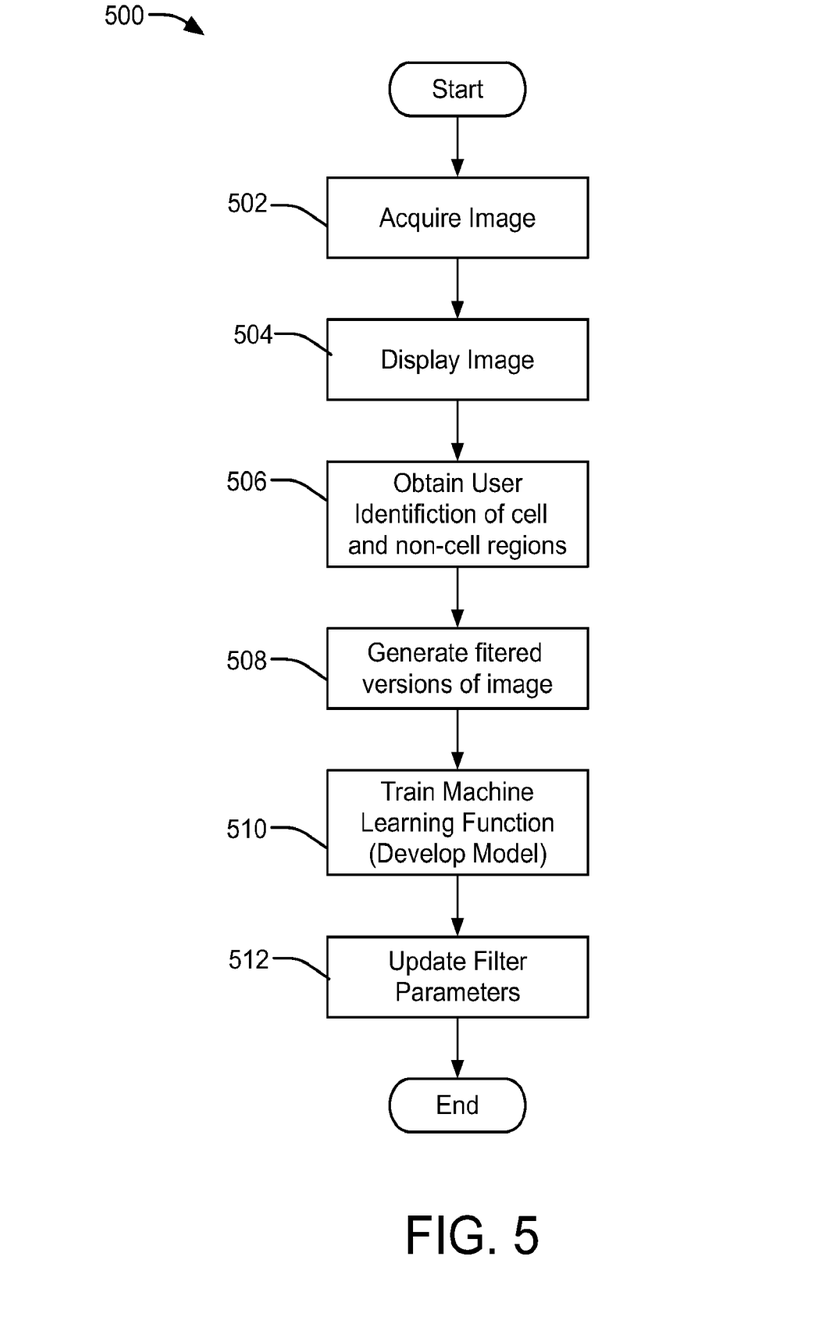
FIG. 5 is a flowchart of processing undertaken by the system of FIG. 1 to train a machine learning function.

FIG. 5 is a flowchart 500 of the processing undertaken by the system 100 to develop a trained model that may be used to classify pixels in an image. At step 502, the image acquisition module 102 acquires an image and stores the image. At step 504, the user interface module 106 displays the acquired image. At step 506, the user interface module obtains, from the computer 108 used by the user, identification of pixels in the display image that are identified with at least one cell and develops the training data. The filtering module 110, at step 508, generates filtered versions of the acquired image. At step 510, the training module 114 uses the training data developed at step 506 and the filtered version of the acquired image developed at step 508 to develop a trained model. In one embodiment, the trained model is developed by using a random forest decision tree technique to identity an optimal decision tree that predicts the training data from the acquired and the filtered versions of the acquired image. In some embodiments, the training module 114 may evaluate the trained model to determine which filtered versions the developed trained model uses. In such embodiments, parameters for the filtering module 110 are updated at step 512 by the training module 114 so that unnecessary filtered versions of subsequent images are not developed.

Figure 6:
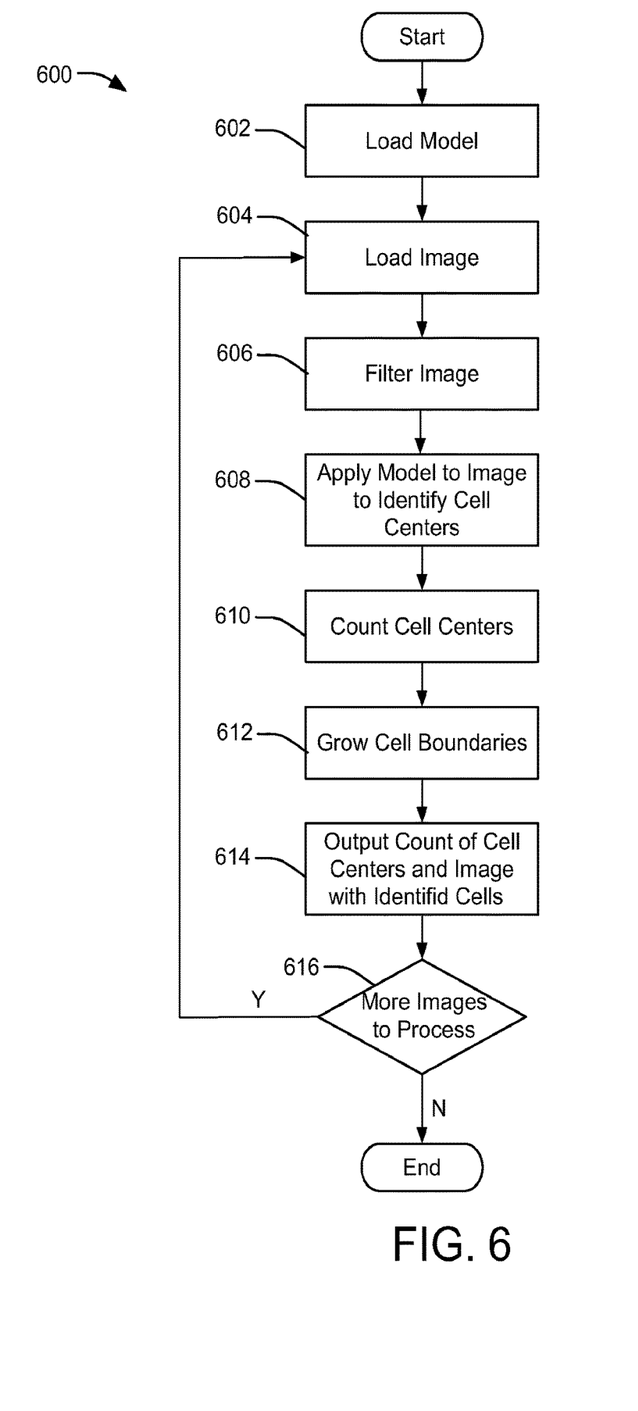
FIG. 6 is another flowchart of processing undertaken by the system of FIG. 1 to apply a trained model developed in FIG. 5 to an image.

FIG. 6 shows a flowchart 600 of the processing undertaken by the system 100 to use the trained model to classify pixels in an image and use such classification to develop statistics of cells in the image. At step 602, the cell identification module 118 loads the trained model developed at step 510 of FIG. 5. At step 604, the image acquisition module 102 acquires an image to be classified. The filtering module 110, at step 606 develops filtered versions of the image to be classified. The cell identification module 118, at step 608, uses the trained model and the filtered versions of the image to be classified to classify pixels in the image. At step 610, the cell measurement module 120, uses the pixel classification developed to count cell centers, at step 608. In addition, in some embodiments, if only cell centers are identified, the cell measurement module 120 may classify pixels surrounding the cell centers as also belonging to a cell, at 612.

At step 614, the cell measurement module outputs the count of the cell centers and an image of the acquired image with the cells identified. At step 616, the image acquisition module 102 determines if there are any additional images to classify and, if so, processing proceeds to step 604 to load a further image. Otherwise, the system 100 exits.

Figure 7:
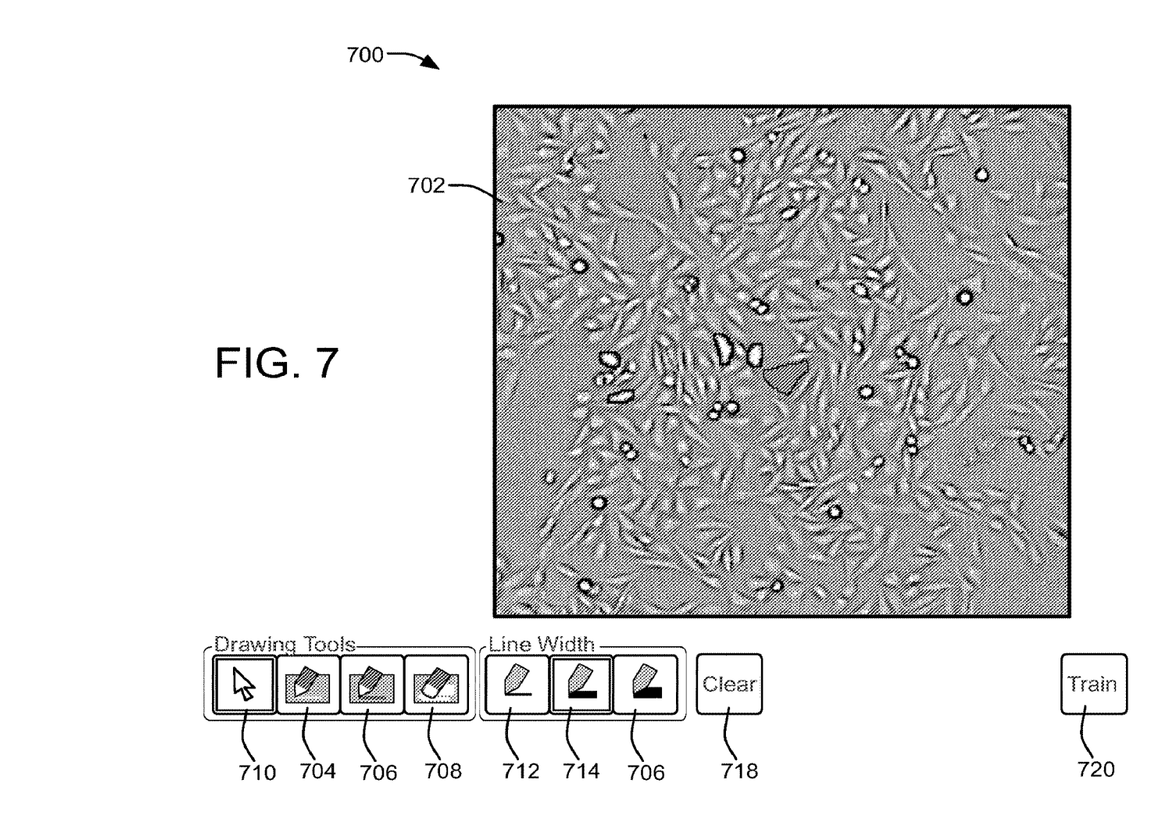
FIG. 7 is a graphical user interface that may be generated by the system of FIG. 1

Referring to FIG. 7, the image classification system 100 may generate a graphical user interface 700 on the display of the computer 107. The graphical user interface 700 includes a region 702 in which an acquired image is displayed and soft buttons 704, 706, 708, and 710. In the exemplary graphical user interface 700, if the user selects the soft button 704 and then selects pixels of the image displayed in the region 702, such pixels will be associated with a cell interior. Similarly, if the user selects the soft button 706 and then selects pixels of the image displayed in the region 702, the selected pixels will be associated with a background of the displayed image or other uninteresting region. It should be apparent, that additional soft buttons may be included in the graphical user interface 700 to allow the user to associate selected pixels of the image with additional pixels. It should also be apparent, that the soft button 704 or 706 may be associated with popup menu that allows the user to identify a feature (e.g., cell center, cell type, cell edge, debris, and the like) and any pixels that are subsequently selected in the image are associated with the identified feature.

If the user selects the soft button 708 and then selects one or more pixels of the displayed image, any features previously associated with any selected pixels are removed. A selection of the soft button 710 by the user clears any selection of the buttons 704, 706, and 708 so that the user may select pixels in the image without associating such pixels with a feature.

Soft buttons 712, 714, and 716 allow the user to select a line width. For example, if the user selects the soft button 714, any subsequent selections inside the region 702 may select, for example, one pixel. If the user selects the soft button 714, any subsequent selections inside the region 702 may select, for example, 3 pixels. If the user selects the soft button 716, any subsequent selections inside the region 702 may select, for example, 5 pixels The graphical user interface 700 also includes a soft button 718 and selection of this button clears any associations the user has made between pixels of the image displayed in the region 702 and features selected using the soft buttons 704 and 706.

After the user has completed associating pixels of the image displayed in the region 702 with features, the user may select a soft button 720 to submit such associations to the user interface module 106 to develop and store training data in the training data store 109. In some embodiments, the user interface 700 calls the training module 114 to begin development of the trained model from the stored training data.

The system 100 may be used to identify objects in images acquired using different modalities, including, transmitted light, fluorescent images, differential interference contrast, phase contrast, brightfield imaging, and the like. The system 100 may be used with images of cells labeled with markers and unlabeled cells. Further, a trained model may be developed using an image acquired using one modality and the training model may be subsequently applied to a image acquired using a different modality.

The system 100 may be used to identify and segment objects in a large scale image, for example, to separate and count sea urchin eggs.

The system 100 may also be used to segment cells in an image, for example, to classify pixels of an image that correspond to mitochondria and the like. The system 100 may be used to classify and distinguish pixels that correspond to different populations of cells in an image, for example, to distinguish pixels associated with neurons from pixels associated with glial cells or pixels associated with live cells from pixels associated with dead cells. The system 100 may be used to identify pixels associated with cells of different populations or the same population that are confluent in the same image.

Although the system 100 above is described in the context of identifying cells in an image, it should be apparent that such system may be used to identify any type of object in an image. The system 100 can be used to identify, from a background, separated objects in an image as well as confluent (or touching) objects in the image. Further, the system 100 may be used to classify pixels that correspond to various types of objects in an image.

It will be understood and appreciated that one or more of the modules, processes, sub-processes, and process steps described in connection with FIGS. 1-7 may be performed by hardware, software, or a combination of hardware and software on one or more electronic or digitally-controlled devices. The software may reside in a software memory (not shown) in a suitable electronic processing component or system such as, for example, one or more of the functional systems, controllers, devices, components, modules, or sub-modules schematically depicted in FIGS. 1-7. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module or controller (e.g., the image acquisition module 102, the user interface module 106, the filtering module 110, the training module 114, the cell identification module 118, and the cell measurement module 120), which includes, for example, one or more microprocessors, general purpose processors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that receiving and transmitting of data as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

INDUSTRIAL APPLICABILITY

Numerous modifications to the present invention will be apparent to those skilled in the art in view of the foregoing description. The method and system described herein may be used to identify objects, in particular cells, in images acquired under various illumination conditions and using different microcopy techniques. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A computer-implemented method of classifying pixels associated with objects in an image, comprising:
   receiving an image;
   receiving training data, wherein the training data identifies a pixel associated with an object of a particular type in the image;
   developing a plurality of filtered versions of the image;
   processing the training data and the plurality of filtered versions of the image to develop a trained model for classifying pixels associated with objects of the particular type;
   applying the trained model to the image to identify pixels associated with a plurality of objects of the particular type in the image; and
   wherein the particular type is a biological cell and applying the trained model identifies pixels associated with boundaries between confluent biological cells in the image.

2. The computer-implemented method of claim 1, further comprising receiving a further image and applying the trained model to the further image to identify pixels associated with a plurality of cells in the further image.

3. The computer-implemented method of claim 2, wherein applying the trained model to the further image comprises developing a plurality of filtered versions of the further image.

4. The computer-implemented method of claim 3, wherein:
   developing each of the plurality of filtered versions of the image comprises applying a filter selected from a first set of filters;
   developing each of the plurality of filtered versions of the further image comprises applying a filter selected from a second set of filters; and
   wherein the first set of filters and the second set of filters are not identical.

5. The computer-implemented method of claim 1, wherein applying the trained model includes using one of a Random Forest Decision Tree algorithm, a neural network, support vector machines, and a k-means clustering algorithm.

6. The computer-implemented method of claim 1, wherein developing a filtered version of the image includes applying one of an edge detection filter, a peak detection filter, a subsampling filter, and a smoothing operator.

7. The computer-implemented method of claim 1, further comprising determining how many cells are represented by the identified pixels associated with the plurality of cells in the image.

8. The computer-implemented method of claim 1, further comprising growing an identified portion of an identified cell to select additional pixels associated with the cell.

9. A system for classifying pixels associated with objects in an image, wherein the system includes one or more processors, comprising:
   a computer-based image acquisition module operating on the one or more processors and configured to receive an image from an image source;
   a computer-based user interface module operating on the one or more processors and configured to receive training data, wherein the training data identifies a pixel associated with an object of a particular type in the image;

a computer-based filtering module operating on the one or more processors and configured to automatically develop a plurality of filtered versions of the image;

a computer-based training module operating on the one or more processors and configured to automatically process the training data and the plurality of filtered versions of the image to develop a trained model for classifying pixels associated with objects of the particular type;

a computer-based object identification module operating on the one or more processors and configured to automatically apply the trained model to the image to identify pixels associated with a plurality of objects of the particular type in the image; and wherein the particular type is a biological cell and wherein the object identification module identifies pixels associated with boundaries between confluent biological cells in the image.

10. The system of claim 9, wherein the computer-based image acquisition module is configured to receive a further image and the computer-based cell identification module is configured to apply the trained model to the further image to identify pixels associated with a plurality of cells in the further image.

11. The system of claim 10, wherein the computer-based filtering module is configured to automatically develop filtered versions of the further image and the computer-based cell identification module is configured to automatically use the filtered versions of the further image to identify pixels associated with the plurality of cells in the image.

12. The system of claim 11, wherein the computer-based filtering module is configured to automatically apply a first set of filters to develop the plurality of filtered versions of the image and to automatically use a second set of filters to develop the plurality of filtered versions of the further image, and wherein the first set of filters and the second set of filters are not identical.

13. The system of claim 9, wherein the computer-based object identification module is configured to automatically use one of a Random Forest Decision Tree algorithm, a neural network, support vector machines, and a k-means clustering algorithm.

14. The system of claim 9, wherein the computer-based filtering module is configured to automatically apply to the image one of an edge detection filter, a peak detection filter, a subsampling filter, and a smoothing operator.

15. The system of claim 9, further comprising a computer-based cell measurement module operating on the one or more processors and configured to automatically determine how many cells are represented by the identified pixels associated with the plurality of cells in the image.

16. The system of claim 9, wherein the computer-based cell measurement module is configured to automatically calculate statistics associated with the plurality of cells in the image.

* * * * *

UNITED STATES PATENT AND TRADEMARK OFFICE
CERTIFICATE OF CORRECTION

PATENT NO. : 9,830,502 B2
APPLICATION NO. : 15/031523
DATED : November 28, 2017
INVENTOR(S) : Avrum Isaac Cohen and Dihui Hong It is certified that error appears in the above-identified patent and that said Letters Patent is hereby corrected as shown below:

On the Title Page

(73) Assignee: "DH Technologies Development Pte. Ltd., Singapore (SG)" should read -- Molecular Devices, LLC, Sunnyvale, CA (US) --

Signed and Sealed this
Twenty-seventh Day of November, 2018

Andrei Iancu
*Director of the United States Patent and Trademark Office*